US011001606B2

(12) United States Patent
Tikhomirov et al.

(10) Patent No.: US 11,001,606 B2
(45) Date of Patent: May 11, 2021

(54) COMPOSITIONS AND METHODS FOR FRACTAL ASSEMBLY OF MICRON-SCALE NUCLEIC ACID STRUCTURES

(71) Applicant: California Institute of Technology, Pasadena, CA (US)

(72) Inventors: Grigory Tikhomirov, Pasadena, CA (US); Philip F. Petersen, Covina, CA (US); Lulu Qian, La Crescenta, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 259 days.

(21) Appl. No.: 16/118,425

(22) Filed: Aug. 30, 2018

(65) Prior Publication Data

US 2019/0062366 A1 Feb. 28, 2019

Related U.S. Application Data

(60) Provisional application No. 62/551,925, filed on Aug. 30, 2017.

(51) Int. Cl.
| | | |
|---|---|---|
| *C12Q 1/68* | (2018.01) | |
| *C07H 21/00* | (2006.01) | |
| *C07H 21/04* | (2006.01) | |
| *B81C 1/00* | (2006.01) | |
| *B81B 1/00* | (2006.01) | |
| *B82B 3/00* | (2006.01) | |

(52) U.S. Cl.
CPC ............. *C07H 21/04* (2013.01); *B81B 1/006* (2013.01); *B81C 1/00007* (2013.01); *B82B 3/0047* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 2005/0218398 | A1* | 10/2005 | Tran ................... | H01L 27/14603 257/14 |
| 2007/0117109 | A1* | 5/2007 | Rothemund ............. | C12P 19/34 435/6.12 |
| 2010/0069621 | A1* | 3/2010 | Maune ...................... | B82B 1/00 536/23.1 |
| 2012/0022244 | A1* | 1/2012 | Yin ......................... | B82Y 40/00 536/23.1 |

OTHER PUBLICATIONS

Andersen et al., Self-assembly of a nanoscale DNA box with a ontrollable lid. Nature 459:73 (Year: 2009).*
Barish et al., An information-bearing seed for nucleating alogrithmic self-assembly. PNAS 106(15) : 6054-6059 (Year: 2009).*
Castro et al., A primer to scaffolded DNA origami. Nature Methods 8(3) :221 (Year: 2011).*
Dietz et al., Folding DNA into Twisted and Curved Nanoscale Shapes. Science 325 : 725 (Year: 2009).*
Doty, D. Theory of Algorithmic Self-Assembly. Communications of the ACM 55(12) : 78 (Year: 2012).*
Gerling et al., Dynamic DNA devices and assemblies formed by shape-complementary,non-base pairing 3D components. Science 347(6229) : 1446 (Year: 2015).*
Han et al., DNA Origami with Complex Curvatures in Three-Dimensional Space. Science 332 : 342 (Year: 2011).*
Han et al., DNA Gridiron Nanostructures Based on Four-Arm Junctions. Science 339 : 1412 (Year: 2013).*
Iinuma et al., Polyhedra Self-Assembled from DNA Tripods and Characterized with 3D DNA-PAINT. Science 344 :65 (Year: 2014).*
Ke et al., Multilayer DNA Origami Packed on a Square Lattice. JACS 131 : 15903 (Year: 2009).*
Ke et al., Multilayer DNA Origami Packed on Hexagonal and Hybrid Lattices. JACS 134 : 1770 (Year: 2012).*
Marcjihi et al., Toward Larger DNA Origami. Nano Letters 14 : 5740 (Year: 2014).*
Rafat et al., Surface-Assisted Large-Scale Ordering of DNA Origami Tiles. Agnew. Chem. Int. Ed. 53 : 7665 (Year: 2014).*
Rothemund et al., Algorithmic Self-Assembly of DNA Sierpinski Triangles. Plos Biology 2 (12) : e424 (Year: 2004).*
Schulman et al., Robust self-replication of combinatorial information via crystal growth and scission. PNAS 109(17) : 6405 (Year: 2012).*
Tikhomirov et al., Programmable disorder in random DNA tilings. Nature Nanotechnology 12 : 251 (Year: 2017).*
Veneziano et al., Designer nanoscale DNA assemblies programmed from the top down. Science 352(6293) : 1534 (Year: 2016).*
Wang et al., The Beayty and Utility of DNA Origami. Chem. 2 :359-382 (Year: 2017).*
Zhang et al., Complex wireframe DNA origami nanostructures with multi-arm junction vertices. Nature Nanotechnology 10 : 779 (Year: 2015).*
Zhao et al., Organizing DNA Origami Tiles into Larger Structures Using PreformedScaffold Frames. Nano Letters 11 : 2997 (Year: 2011)*
Douglas et al., "Rapid prototyping of 3D DNA-origami shapes with caDNAno," Nucleic Acids Research, vol. 37, No. 15, 2009, pp. 5001-5006.
Gerling et al., "Sequence-programmable covalent bonding of designed DNA assemblies," Sci. Adv., vol. 4, Aug. 17, 2018, pp. 1-11.
Knudsen et al., "Routing of individual polymers in designed patterns," Nature Nanotechnology, vol. 10, Oct. 2015, pp. 892-898.

(Continued)

*Primary Examiner* — Ethan C Whisenant
(74) *Attorney, Agent, or Firm* — Lewis Roca Rothgerber Christie LLP

(57) ABSTRACT

Compositions and methods of the present disclosure provide for staged assembly of nucleic acid microstructures made of an array of x number of polynucleotide tiles, where each of the polynucleotide tiles is a polygon configuration and is made from a single-stranded helical polynucleotide scaffold and a plurality of single-stranded polynucleotide staple strands of y number of unique staple sequences corresponding to the selected tile configuration, the y number of unique staple sequences capable of being constant for any value of x.

4 Claims, 11 Drawing Sheets
(6 of 11 Drawing Sheet(s) Filed in Color)

(56) References Cited

OTHER PUBLICATIONS

Maune et al., "Self-assembly of carbon nanotubes into two-dimensional geometries using DNA origami templates," *Nature Nanotechnology*, vol. 5, Jan. 2010, pp. 61-66.

Petersen, P. 2017, *FracTile Compiler* http://gianlab.caltech.edu/FracTileCompiler (online software available free of charge).

Rinker et al., "Self-assembled DNA nanostructures for distance-dependent multivalent ligand-protein binding," *Nature Nanotechnology*, vol. 3, Jul. 2008, pp. 418-422.

Rothemund, "Folding DNA to create nanoscale shapes and patterns," *Nature*, vol. 440, No. 16, 2006, pp. 297-302.

Schreiber et al., "Hierarchical assembly of metal nanoparticles, quantum dots and organic dyes using DNA origami scaffolds," *Nature Nanotechnology*, vol. 9, Jan. 2014, pp. 74-78.

Tikhomirov et al., "Fractal assembly of micrometer-scale DNA origami arrays with arbitrary patterns," *Nature*, vol. 552, Dec. 7, 2017, pp. 67-71.

Tikhomirov et al., "Fractal assembly of micrometer-scale DNA origami arrays with arbitrary patterns," Supplementary Information; DOI: 10.1038/nature24655, pp. 1-51.

Tikhomirov et al., "Programmable disorder in random DNA tilings," *Nature Nanotechnology*, DOI:10.1038/NNANO.2016.256, pp. 1-10.

Tikhomirov et al., "Triangular DNA origami tilings," Bioengineering, Biology and Computer Science, California Institute of Technology, Pasadena, CA 91125, USA.

\* cited by examiner

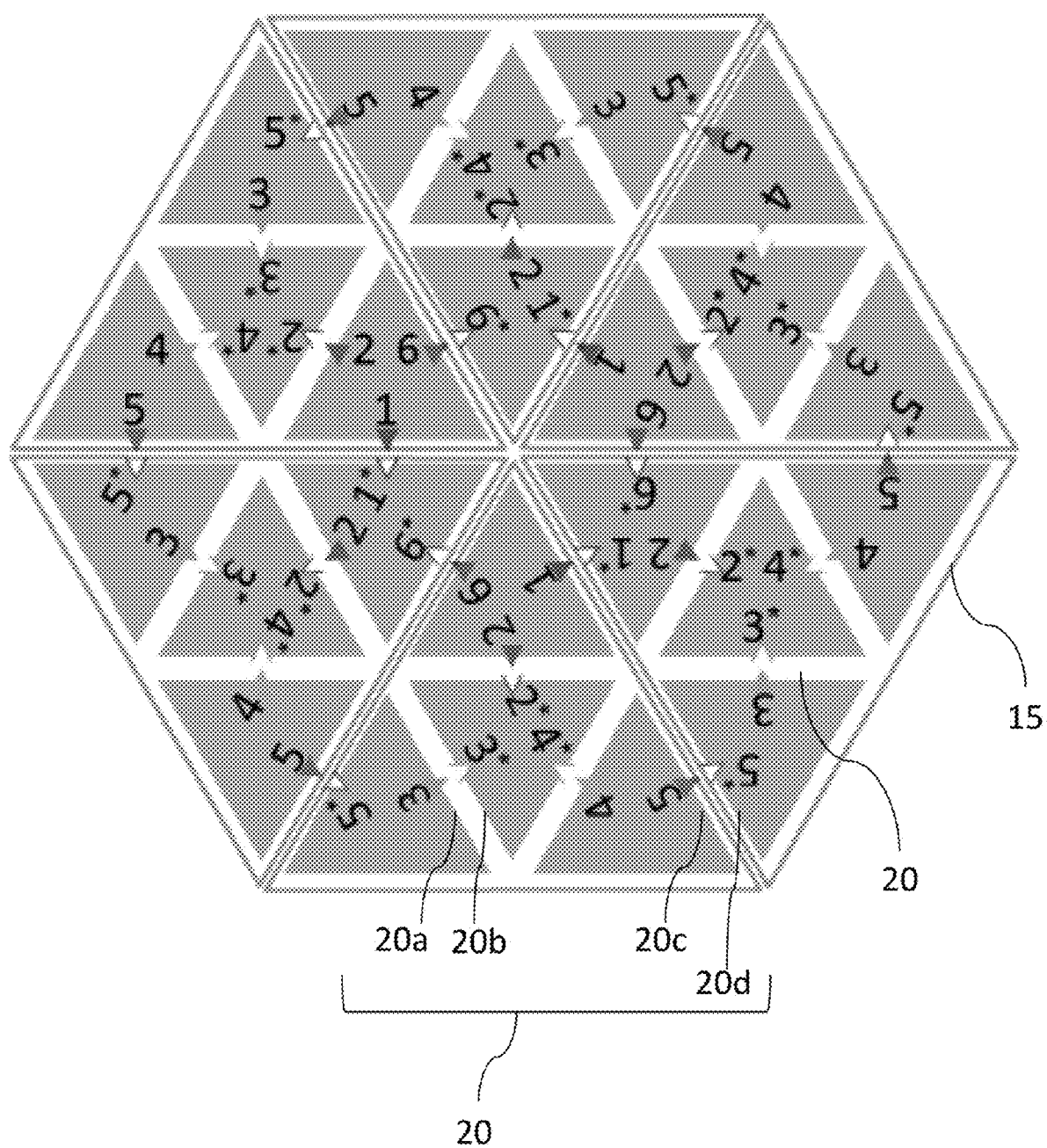

20  15

Modified edge staple strands

COMPOSITIONS AND METHODS FOR FRACTAL ASSEMBLY OF MICRON-SCALE NUCLEIC ACID STRUCTURES

CROSS-REFERENCE TO RELATED APPLICATION

The present application claims priority to and the benefit of U.S. Provisional Application Ser. No. 62/551,925 filed on Aug. 30, 2017, entitled "Fractal Assembly of Micron-Scale Uniquely-Addressable DNA Origami Assays," the entire content of which is incorporated herein by reference.

STATEMENT REGARDING FEDERALLY SPONSORED RESEARCH OR DEVELOPMENT

This invention was made with government support under Grant No. GM007616 awarded by the National Institutes of Health and under Grant No. CCF1317694 and Grant No. CCF1351081 awarded by the National Science Foundation. The government has certain rights in the invention.

BACKGROUND

Self-assembled deoxyribonucleic acid (DNA) nanostructures enable nanometer-precise patterning that may be used to create programmable molecular machines and arrays of functional materials. DNA origami is the nanoscale folding of DNA to create non-arbitrary two- and three-dimensional shapes which is particularly versatile in the context of programmable molecular machines and arrays because each DNA staple strand in the origami nanostructure occupies a unique position and can serve as a uniquely addressable pixel. However, the scale of such structures has been limited to about 0.05 square micrometres, hindering applications that demand a larger layout and integration with more conventional patterning methods.

SUMMARY

Aspects of embodiments of the present disclosure are directed to compositions and methods of the present disclosure provide for staged assembly of nucleic acid microstructures made of an array of x number of polynucleotide tiles, where each of the polynucleotide tiles is a polygon configuration and is made from a single-stranded helical polynucleotide scaffold and a plurality of single-stranded polynucleotide staple strands having y number of unique staple sequences corresponding to the selected tile configuration, the y number of unique staple sequences capable of being constant for any value of x.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, together with the specification, illustrate example embodiments of the present disclosure, and, together with the description, serve to explain the principles of the present disclosure.

FIG. 2A is a schematic of hexagonal array made of triangular polynucleotide tiles having an inert exterior edge, according to embodiments of the present disclosure.

DETAILED DESCRIPTION

Figure 1:
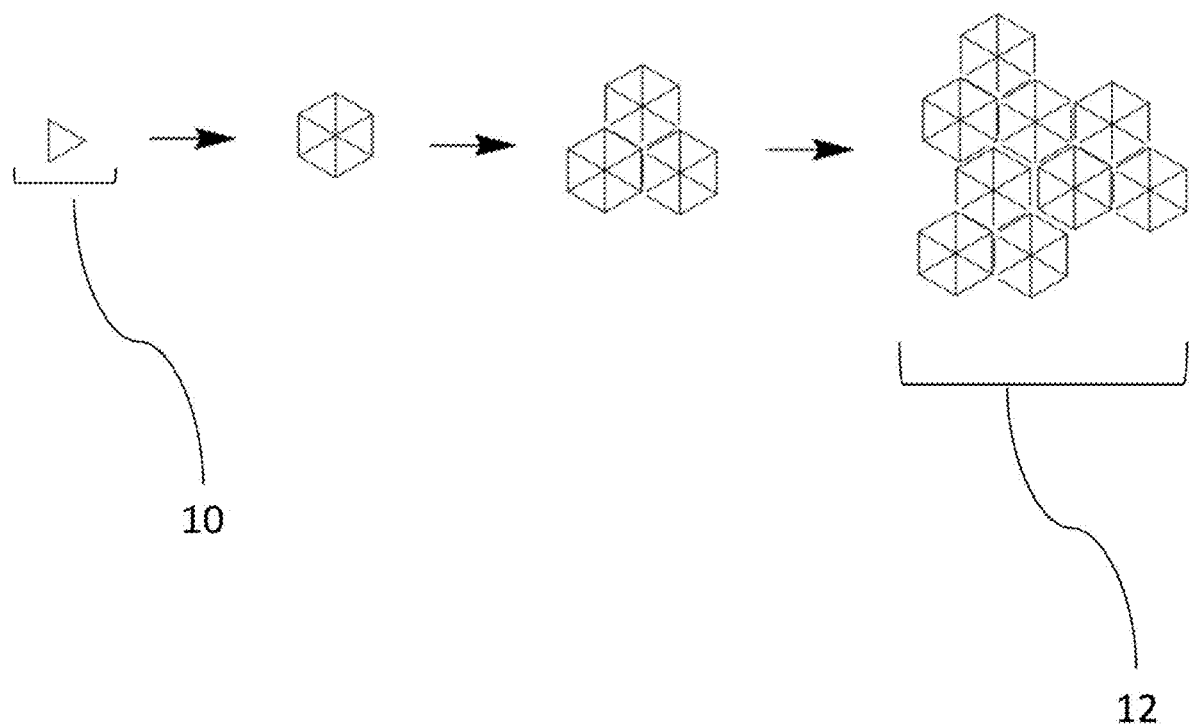
FIG. 1 is a schematic depicting assembly of triangular polynucleotide tile array, according to embodiments of the present disclosure.

The field of DNA origami has provided a malleable substrate with a multitude of options for carving out a desired nucleic acid platform structure. The basic DNA origami materials include a long single-stranded polynucleotide scaffold that may be folded (like origami paper) using shorter polynucleotide staple strands. See, e.g., Rothemund, 2006, *Nature*, 440:297-302, the entire contents of which are incorporated herein by reference.

The present disclosure provides a straightforward and modular approach for self-assembly of a nucleic acid nanostructure from an array of polynucleotide tiles. Methods of the present disclosure include implementing modified assembly rules recursively throughout a hierarchical, multistage assembly process to create assembled polynucleotide tile arrays of micrometer size. Additionally, these micrometer nucleic acid structures are capable of presenting arbitrary patterns using a constant set of unique polynucleotide strands.

Following methods according to embodiments of the present disclosure, nucleic acid structures may be prepared in a modular protocol for self-assembly of multiple monomer polynucleotide tiles where each tile is made from the same selected polynucleotide scaffold folded with the same unique set of polynucleotide staple strands. By using the same scaffold and unique staple strands for each monomer tile, a micrometer-size nucleic acid structure may be assembled without the need to design additional scaffolds and/or multiple sets of unique polynucleotide strands, thereby significantly reducing the cost and time for designing and producing the microstructures. As described in more detail throughout this disclosure, the step-wise assembly of these monomer tiles is directed by modifying the polynucleotides at the edges of the monomer tiles to create sets of tiles with edges of different bonding energies thereby controlling the tiles which are capable of linking together via their modified edges using different annealing temperatures.

Furthermore, arbitrary patterns may be incorporated into the disclosed nucleic acid structures without any significant effect on the assembly method or the size of the assembled structure. As each monomer tile includes polynucleotide staple strands of known sequences, these nucleotide sequences may be manipulated (e.g., modified or extended) to create binding sites (also referred to as pixels) available for attachment of desired molecules, moieties, and/or particles. Specifically, the 5' and 3' end of each interior staple strand may be conjugated directly to or extended as attachment sites for molecules including proteins, carbon nanotubes, polymers, metal nanoparticles and organic dyes as described in Rinker et al., 2008, *Nat. Nanotechnol.*, 3:418-422; Maune et al., 2010, *Nat. Nanotechnol.*, 5:61-66; Knudsen et al., 2015, *Nat. Nanotechnol.*, 10:892-898; and Schreiber et al., 2014, *Nat. Nanotechnol.*, 9:74-78, respectively, the entire contents of all of which are incorporated herein by reference.

As used herein, "polynucleotide" refers to a polymer of nucleotide monomers covalently bonded. Examples of polynucleotides include single stranded (ss) deoxyribonucleic acid (DNA) (ssDNA) and ribonucleic acid (RNA). The present disclosure uses and discusses ssDNA as an example polynucleotide in the assembly of a nucleic acid array structure. However, embodiments of the present disclosure include assembly of other polynucleotide tiles having purine and pyrimidine bases including RNA and peptide nucleic acids (PNA) as well as other natural, chemically or biochemically modified, non-natural, or derivatized. The backbone of the polynucleotide may include sugars and phosphate groups as found in RNA or DNA or may be modified or substituted sugar or phosphate groups. A polynucleotide may include modified nucleotides such as methylated nucleotides and nucleotide analogs.

As used herein "scaffold," "polynucleotide scaffold," "single-stranded polynucleotide scaffold," "single-stranded helical polynucleotide scaffold," "scaffold strand," and like terms are used interchangeably to refer to a long single-stranded helical polynucleotide scaffold of a known sequence. In some embodiments, the single-stranded polynucleotide scaffold is at least 1,500 base pairs in length. An example polynucleotide scaffold used in the examples of the present disclosure is a single-stranded DNA scaffold strand derived from M13mp18 DNA. A representation of a folded M13mp18 polynucleotide scaffold 25 is shown in black in FIG. 3. This M13mp18 scaffold of 7,249 bases pairs may be purchased from Bayou Biolabs (Catalog number P-107). In some embodiments of the present disclosure, it may be necessary or preferred to not use the entire M13mp18 single stranded sequence as it may be necessary to remove interfering sequences depending on the selected array configuration and the selected polynucleotide tile configurations therein. Accordingly, an M13mp18 scaffold may be derived from the complete M13mp18 single-stranded sequence.

As used herein, "polynucleotide staple strand," refers to a short single strand of nucleic acids (e.g., ssDNA) that hybridize to (i.e., are complementary to) a region of the scaffold strand the binding of which results in (or is calculated to result in) the folding ("stapling") of the scaffold strand into a desired configuration. This nucleic acid strand folding technique is referred to as DNA origami as described in Rothemund, 2006, supra. A "plurality of polynucleotide staple strands" refers to at least a set of polynucleotide staples strands calculated or computed to fold a polynucleotide scaffold into a selected configuration or array configuration. According to embodiments of the present disclosure, after a configuration (e.g., an array configuration) is selected and entered (e.g., a desired image is uploaded) into a computer software program as disclosed herein, the computer program generates (e.g., computes) a corresponding set of polynucleotide staple strand sequences for binding to and folding the selected scaffold strand into the selected configuration.

As used herein, "tile" or "polynucleotide tile" refers to the folded configuration (i.e., folded/stapled configuration) of a polynucleotide scaffold and a corresponding plurality of polynucleotide staple strands. This tile may also be referred to as a monomer of a configuration, a monomer of an array, a monomer polynucleotide tile, or a monomer tile or a single tile with respect to an assembled configuration. According to some embodiments of the present disclosure, each monomer tile has 3 or more edges and at least one edge of each tile is capable of linking or pairing with an edge of another tile. Examples of a monomer tile 10 is shown as a triangular configuration in FIG. 1 and a square configuration in FIG. 3.

As used herein, a "configuration," refers to the selected design rendered by or to be rendered by the selected polynucleotide scaffold complexed with the plurality of polynucleotide staple strands. In some embodiment, the configuration also includes any modifications or extensions made to pixelate (e.g., add binding sites to) the tiles of the array. As disclosed herein configuration may refer to a "tile configuration" or an "array configuration." A tile configuration refers to the design conferred by the scaffold and staple strands of a monomer tile including any pattern pixels and an array configuration refers to the design conferred by the assembly of multiple monomer tiles which may also include any pattern pixels. For example, with reference to FIG. 1, the tile configuration of tile 10 is a triangle and the array configuration 12 is a random assembly of the triangular tiles. With reference to FIG. 2A, the tile configuration is a triangle and the array configuration is a hexagon. With reference to FIG. 3, the tile configuration of tile 10 is a square. As shown specifically in FIG. 3, the tile configuration of the folded scaffold 25 (shown in black) with "edge staple strands" 30 shown in blue, "interior staple strands" 35 shown in green, and "bridge staple strands" 40 shown in orange is not necessarily a true square. The variation of any tile configuration such as a triangle or square with respect to being or approximating a true triangle or true square will depend on the selected scaffold as well as the staple strands. However, in some embodiments, the outer "edge staple strands" 30 form a collective edge 45 which if extended for all collective edges 45 as depicted by the dashed red line 50 will form intersecting lines thereby forming polygon shape. Accordingly, while the breadth of a collective edge 45 may vary for any tile configuration, the extended edge lines will form a polygon configuration.

As used herein, "tile edge staple strands" and "edge staple strands" in the context of a monomer tile 10 refer to the polynucleotide staple strands computed to be positioned at the outer folds of the selected polynucleotide scaffold. With reference to FIG. 3, tile edge staple strands 30 are positioned on the outermost border of a monomer tile. In some embodiments, some of the tile edge staple strands 30 of a monomer tile are modified to form an inert edge thereby rendering the edge incapable of linking with an edge of another monomer tile or with any active polynucleotides in the same tile. Any suitable modification of the polynucleotide edge strand may be used to inhibit or decrease the chances of the edge being capable of binding. Non-limiting examples of modifications for rendering the edge inert include extensions of the edge polynucleotide to form a nucleotide hairpin complex and/or the addition of a poly-thymine (polyT) tail. While one type of modification may be used throughout all of the edge staples along the entire collective edge, it is also possible to use a combination of modifications for making the tile edge staple strands inert.

Figure 2B:
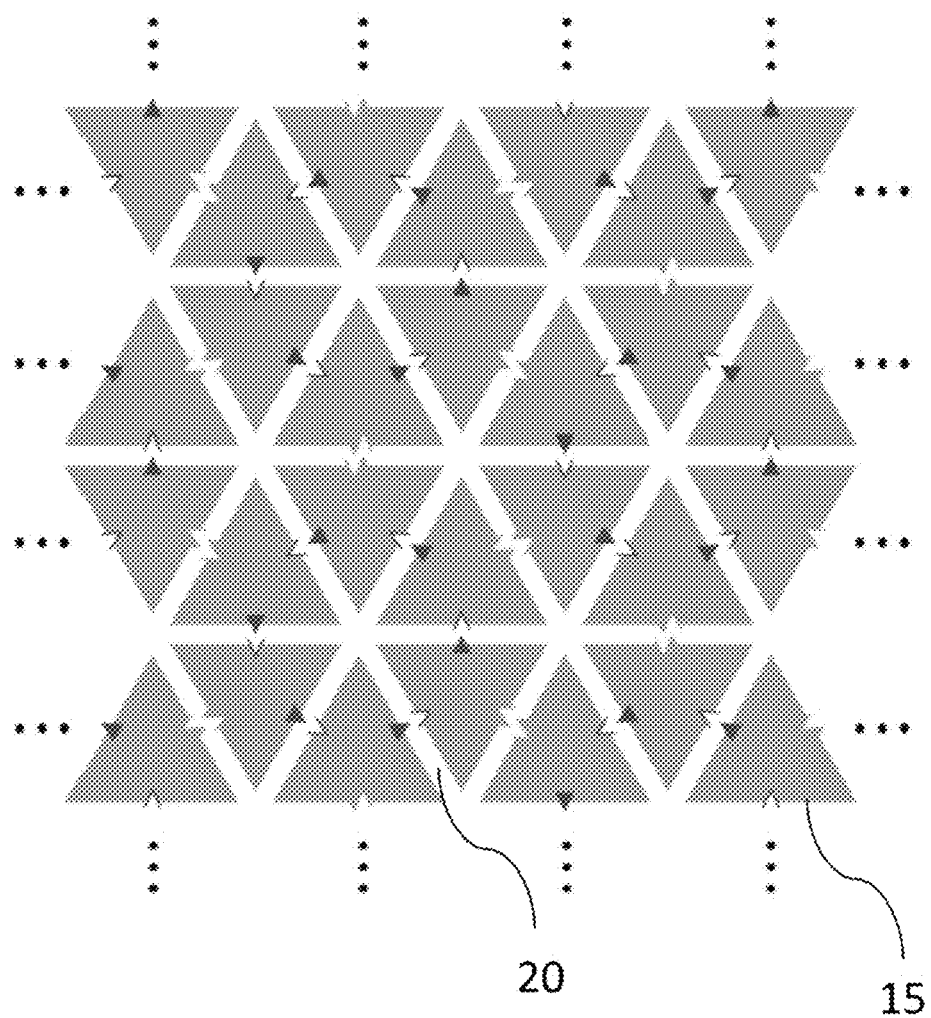
FIG. 2B is a schematic of an unbound array made of triangular polynucleotide tiles having an unbound exterior edge, according to embodiments of the present disclosure.
Figure 3:
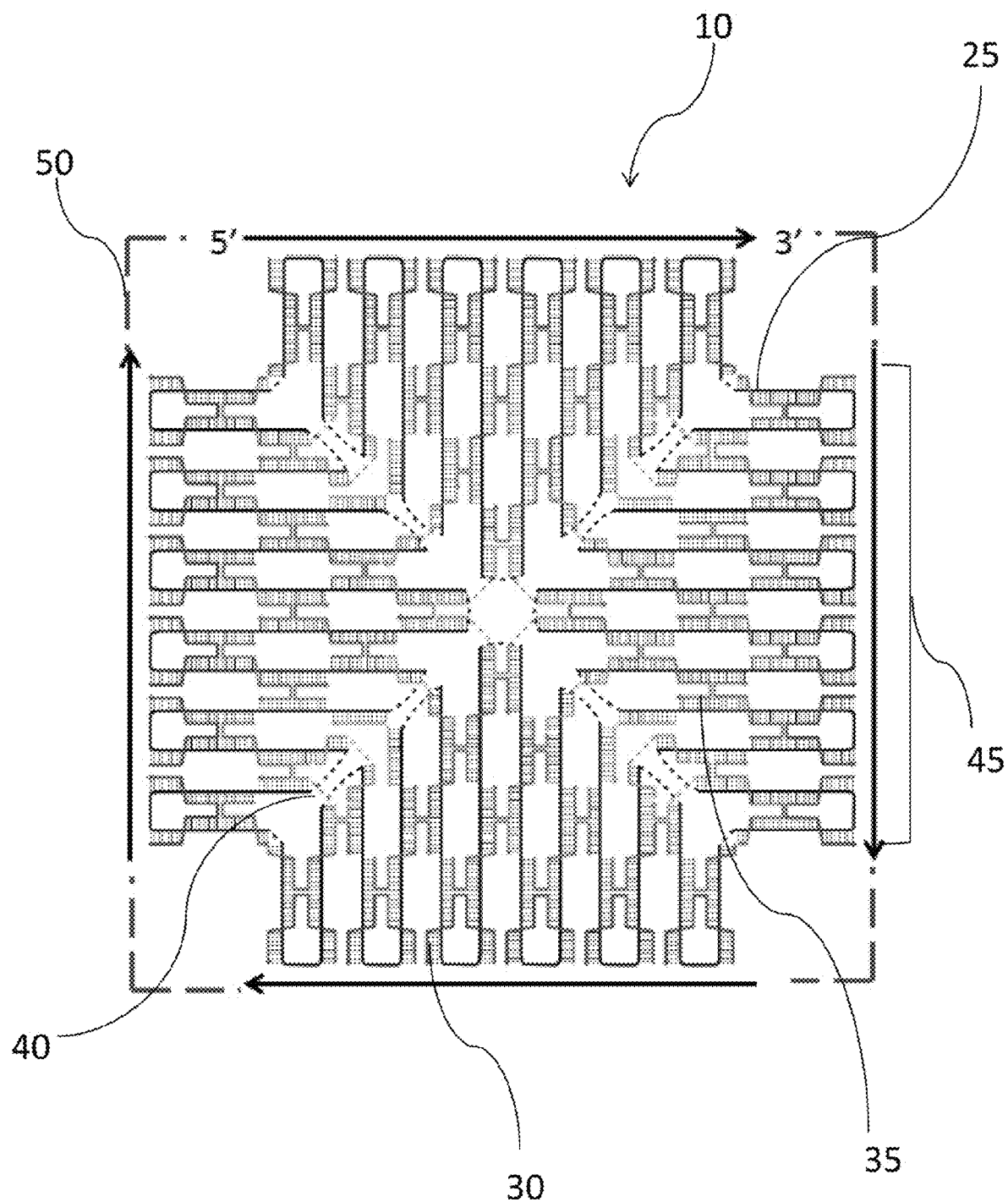
FIG. 3 is a schematic of a monomer square tile 10, according to embodiments of the present disclosure.

With reference to the hexagon array of FIG. 2A, an interior edge 20 is defined as being an edge of a tile that is interior with respect to the entire assembled array with an exterior edge 15 being an edge of a tile that forms the outermost perimeter of the array. In some embodiments, exterior edges 15 may be inert or unbounded. In some embodiments, all or some of the perimeter of the array may be inert. If the perimeter of the array is inert, then the exterior edges 15 of the tiles that form the perimeter are not capable of linking to an edge of another tile. If the entire perimeter of the array is "bounded" then then all of the edges of the tiles that form the perimeter are inert. For example, the hexagon array shown in FIG. 2A is bounded thereby prohibiting additional self-assembly of monomer tiles to this 24 tile hexagon. Alternatively, with reference to FIG. 2B the exterior edges 20 of an assembled array may "unbound," and therefore capable of being linked to additional monomer tiles.

According to embodiments of the present disclosure, the method for assembly of an array of monomer tiles is predicated on designing at least some of the tile edge staple strands for interior edges of the tiles to have different binding energies thereby allowing for directed (e.g., controlled) linking of tiles designed to be linked in a first stage while preserving the binding of the linked tiles during the annealing and linking of subsequent tiles. For example, with continued reference to FIG. 2A, the interior edges 20a, 20b, 20c, and 20d have modified edge staple strands that allowed for linking (i.e., binding) to the edge of the adjacent tile. However, the binding energy (3/3*) required for edge 20a to bind to edge 20b is significantly higher than the binding energy (5/5*) required for edge 20c to bind to edge 20d. In order to prohibit binding of the modified edge staple strands with scaffold strands of other tiles upon mixing of the monomer tiles, negation strands with sequences complementary to the modified edge staples strands are added to each monomer tile.

As used herein, an "array" refers to two or more assembled monomer tiles. An array may be formed of x number of monomer polynucleotide tiles where each monomer polynucleotide tile is formed from the same polynucleotide scaffold strand and computed plurality of polynucleotide staples strands forming a polygon configuration having three or more edges. In some embodiments, x may be any number of total polygon polynucleotide tiles as disclosed herein. In some embodiments, x may be any number of the disclosed polynucleotide tiles that may be assembled into an array in a series of tile binding stages in which each stage directs binding of designated tiles having modified edges to render similar binding energies during which tile edges not designated to bind during a given stage either require a higher annealing temperature (i.e., have a higher binding energy) or are protected (or concealed) from binding using negation strands. In some embodiments, an array of x number of monomer polynucleotide tiles may be assembled according to embodiments of the present disclosure where x may range from 2 to 64.

According to embodiments of the present disclosure, a method for assembling a nucleic acid microstructure made of an array of x number of polynucleotide tiles includes designing the configuration of the desired array. In some embodiments, a tile configuration (polygon shape having 3 or more edges, e.g., a triangle or a square) is selected followed by the overall size of the desired array and a desired arbitrary pattern to be displayed on the array. Using these design features, a suitable computer software program may be used to integrate the design steps from the arbitrary pattern into polynucleotide staple sequences for a selected polynucleotide scaffold (e.g., the FracTile Compiler as disclosed in Petersen, P. 2017, *FracTile Compiler* http://qian-lab.caltech.edu/FracTileCompiler, the entire contents of which are incorporated herein by reference. Additional software programs for computing staple strands for a given scaffold are known and available in the art. For example, caDNAno as described, e.g., in Douglas et al., 2009, *Nucleic Acids Research*, 37:5001-5006, the entire contents of which is incorporated herein by reference.

In order to assemble the monomer tiles as disclosed herein in a directed manner, the linking of tiles is performed in stages in which the first linking stage has the highest binding energy requirement (i.e., highest melting temperature ($T_m$) required to anneal the desired tile edges). In general, a designated number of stages of distinct annealing temperatures for directed tile binding may be represented by:

$$T_m(\text{monomer}) > T_m(\text{Stage 2}) > T_m(\text{Stage 3}) > \ldots > \text{room temperature (25° C.)}.$$

To design the stages with decreasing annealing temperatures while effectively directing the linking of desired tiles, each of the monomer tiles in the array configuration is assigned a relevant stage for binding. This assignment may be performed manually or using any suitable computer program. Accordingly, each monomer tile in the array configuration is assigned a unique position in the array and is assigned a stage for edge binding. With an assigned stage for each monomer tile, the corresponding modifications to the linking edge of each tile are designed and/or assigned. As such, a number and type of edge staple strand for each pairing edge of each monomer tile in the array is determined.

In order to accommodate larger arrays which require multiple stages and therefore multiple distinct edge binding energies, edge designs requiring a narrow range of melting temperatures will increase the number of possible stages. Similarly, the type of edge strand modification influences the range of melting temperatures for any given edge. In some embodiments of the present disclosure, edge staple strands for tile linking may include nucleotide extensions of the edge strand on one pairing edge with a nucleotide truncation on the corresponding pairing edge. Another modification includes blunt end stacking of paired edge staple strands. In some embodiments, a collective edge 45 of a monomer tile may include multiple edge staple strands for tile linking in which each of the edge staple strands on one edge may the same or different. The edge staple strands including nucleotide extensions and truncations as well as blunt end stacking have a sequence dependent on the scaffold strand sequence. In some embodiments, monomer tiles may be modified to have extended edges in order to specifically design sequences for edge staples having selected binding energies. Methods for extending edges of tiles is described in Tikhomirov et al., 2017, *Nat. Nanotechnol.*, DOI:10.1038/NNANO.2016.256, the entire contents of which are incorporated herein by reference. Additionally, in some embodiments, monomer tiles may be modified by introducing covalent bonds into the scaffold structure as described in Gerling et al., 2018, *Science Advances*, DOI:10.1126/sciadv.aau1157, the entire contents of which are incorporated herein by reference.

In some embodiments a polynucleotide tile array may be represented by $m^k$ in which m is the number of smaller sub-arrays assembled into a larger array at each stage and k is the number of stages. In some embodiments, a polynucleotide tile array represented by $m^k$ includes tiles having a configuration of a square, triangle, or hexagon. In some embodiments, a $m^k$ tile array has tile configuration of squares or triangles where m is 2, 3, or 4 and k is 2 or 3. In some embodiments, a $m^k$ tile array has tile configurations of hexagons and m is 2, 3, 4, 5, 6, or 7 and k is 2.

Figure 5A:
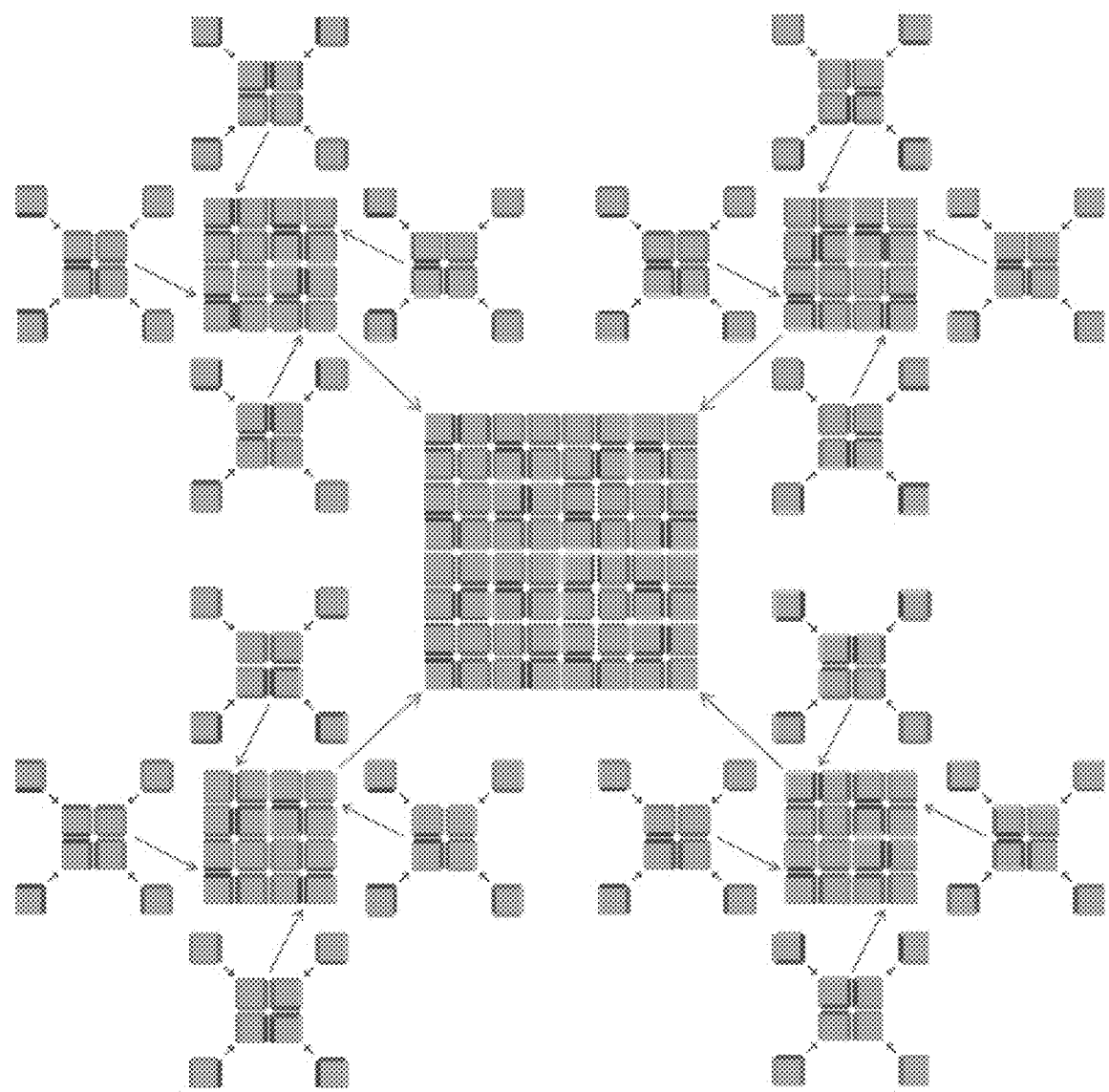
FIG. 5A depicts a 3 stage self-assembly of square tile array as described herein according to embodiments of the present disclosure.
Figure 5B:
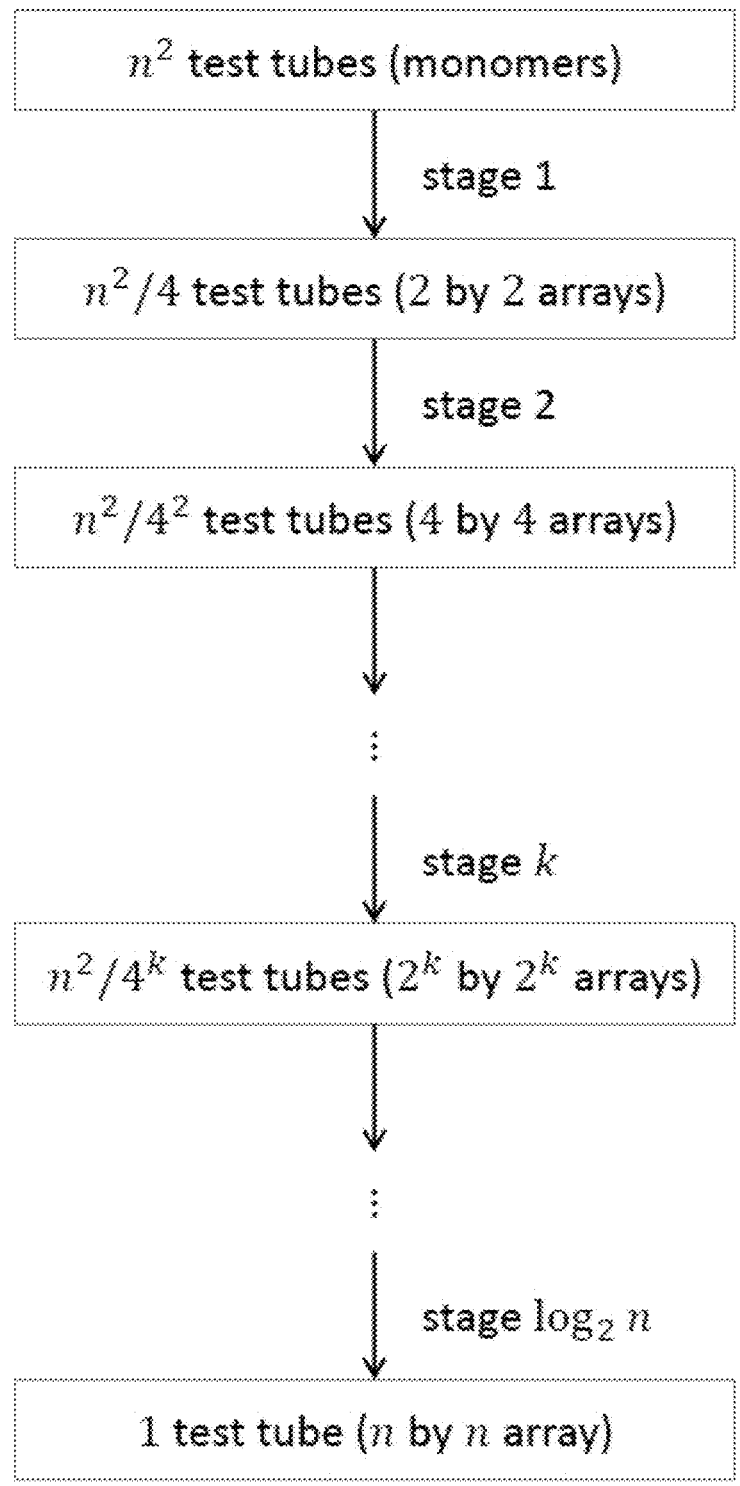
FIG. 5B depicts an outline of for creating n×n square tile arrays in log 2 n stages, according to embodiments of the present disclosure.
Figure 5C:
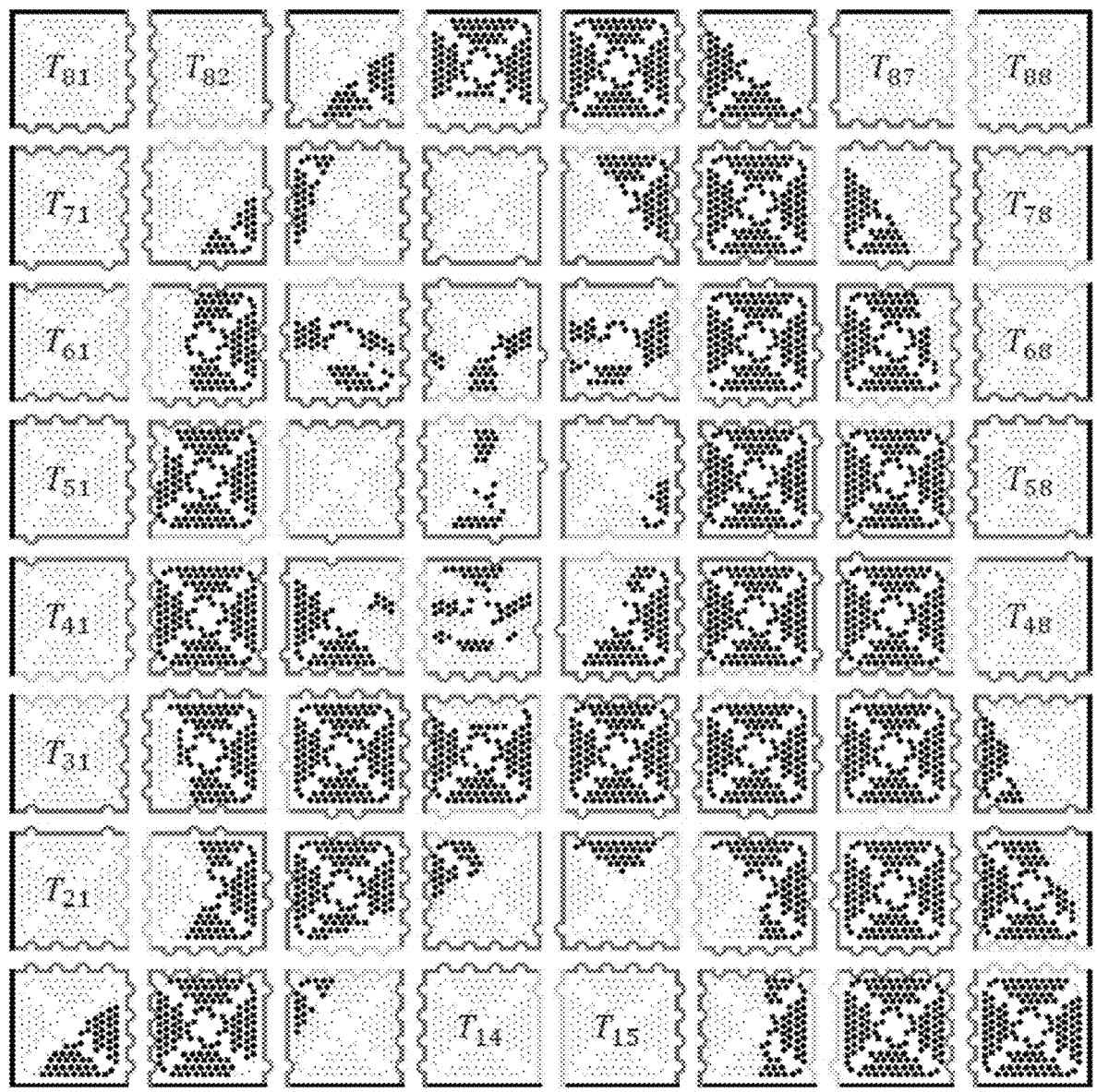
FIG. 5C is a schematic of an 8×8 square tile array with an example pattern of Mona Lisa as described herein according to embodiments of the present disclosure.

As used herein, the computed step-wise methodology of the present disclosure is referred to as "fractal assembly," which is capable of producing nucleic acid array structures (e.g., DNA origami) with sizes up to 0.5 square micrometers with up to 8,704 pixels as depicted in FIG. 5C.

Fractal assembly meets these challenges by being hierarchical and self-similar, such that remarkably complex structures can be produced using simple algorithms with identical rules repeated at different scales. Self-similarity is advantageous because it enables: the creation of structures of increasing size from a small, constant number of unique strands; the implementation of a multistage annealing protocol that works in practice; and the possibility of transferring assembly principles learned when working on smaller structures to the assembly of larger structures. The disclosed fractal assembly method of the square tiles into the arrays is unaffected by changes in surface patterns on the tiles, and that the yield of the fractal assembly process corresponds to about $0.95^{m-1}$ for arrays containing m tiles. When used in conjunction with a software tool that converts an arbitrary pattern into DNA sequences and experimental protocols, our assembly method is readily accessible and will facilitate the construction of sophisticated materials and devices with sizes similar to that of a bacterium using DNA nanostructures.

As used herein a substrate or surface upon which a polynucleotide scaffold is generated can be any substrate or surface that does not result in the degradation of the underlying nucleic acid structure. Typically the substrate or surface will comprise a charge particular of the type of application and/or ligand to be used or attached to the scaffold. Examples of suitable substrates and surfaces include, but are not limited to, glass, mica, polystyrene, polypropylene, stainless steel, silicon and the like.

The surface/substrate used in the methods, compositions and systems of the invention can be made of any material suitable attaching polynucleotides (e.g., such as those used in DNA microarray technology). For example, the substrate can be a material that can be easily sterilized such as plastic or other artificial polymer material. Any number of materials can be used to form the substrate/surface, including, but not limited to, polyamides; polyesters; polystyrene; polypropylene; polyacrylates; polyvinyl compounds (e.g. polyvinylchloride); polycarbonate (PVC); polytetrafluoroethylene (PTFE); nitrocellulose; cotton; polyglycolic acid (PGA); cellulose; dextran; gelatin, glass, fluoropolymers, fluorinated ethylene propylene, polyvinylidene, polydimethylsiloxane, polystyrene, and silicon substrates (such as fused silica, polysilicon, or single silicon crystals), and the like. Also metals (gold, silver, titanium films) can be used.

The following examples are presented for illustrative purposes only, and do not limit the scope or content of the present application.

EXAMPLES

Example 1

Square tile arrays assembled using fractal assembly as shown in FIG. 5C and disclosed in Tikhomirov et al. 2017, *Nature*, DOI: 10.1038/nature24655, the entire contents of which is incorporated herein by reference.

The assembly of individual tiles is designated as stage 0, and the assembly of four square tiles into a 2×2 square array as stage 1 as shown in FIG. 5A. In each subsequent stage, a larger square array is always self-assembled from four smaller arrays that are the products of the previous stage. To create an n×n array, the procedure starts with $n^2$ test tubes of tiles as monomers. Molecules from four such test tubes are combined and self-assembly is allowed to take place at each stage, until all molecules are mixed together in one test tube after log 2 n stages as outlined in FIG. 5B. If each tile has x uniquely addressable pixels, then the final product will have $x \times n^2$ pixels, and each pixel will have a unique address that is determined by the identity of an initial test tube (Tij, where 1 less than or equal to i, j is less than or equal to n) and of the pixel on the tile in that test tube as shown in FIG. 5C.

Figure 5D:
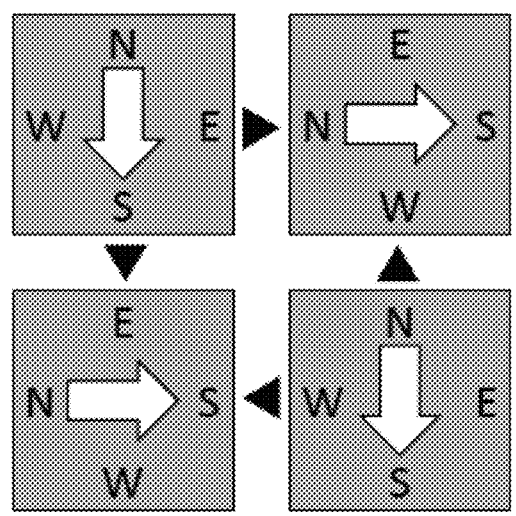
FIG. 5D is a schematic of the giving and receiving rule as described herein according to embodiments of the present disclosure.

Following fractal assembly of square tile array assembly, three embodiments may be applied recursively to all stages of the fractal assembly process. The first embodiment is the 'giving and receiving' rule, which defines the hybridization interactions between DNA origami tiles that are programmed with nucleotide extensions (referred to as the 'giving' edge) and truncations (the 'receiving' edge), the sequences of which depend on the M13 scaffold sequence near the four edges of the square tile. The rule for assigning giving and receiving edges is shown in FIG. 5D for each of the four tiles or arrays, the two interactive edges—which are designed to participate in a given stage of the self-assembly—are either both giving or both receiving. The purpose of this assignment is to reduce self-aggregation because the spurious interactions between non-complementary giving and receiving edges are stronger than those between one of the giving or receiving edges alone.

The second embodiment is the 'rotation' rule, which requires that in each assembly of four tiles or four arrays, two tiles or arrays have one orientation while the other two are rotated 90° relative to the first pair FIG. 5D. Accordingly, if the DNA origami tiles have any internal curvature, it will not be propagated to cause more substantial global curvature in larger arrays. The orientations also allow the four pairs of tile—tile or array—array interactions to be distinct from one another.

Figure 4A:
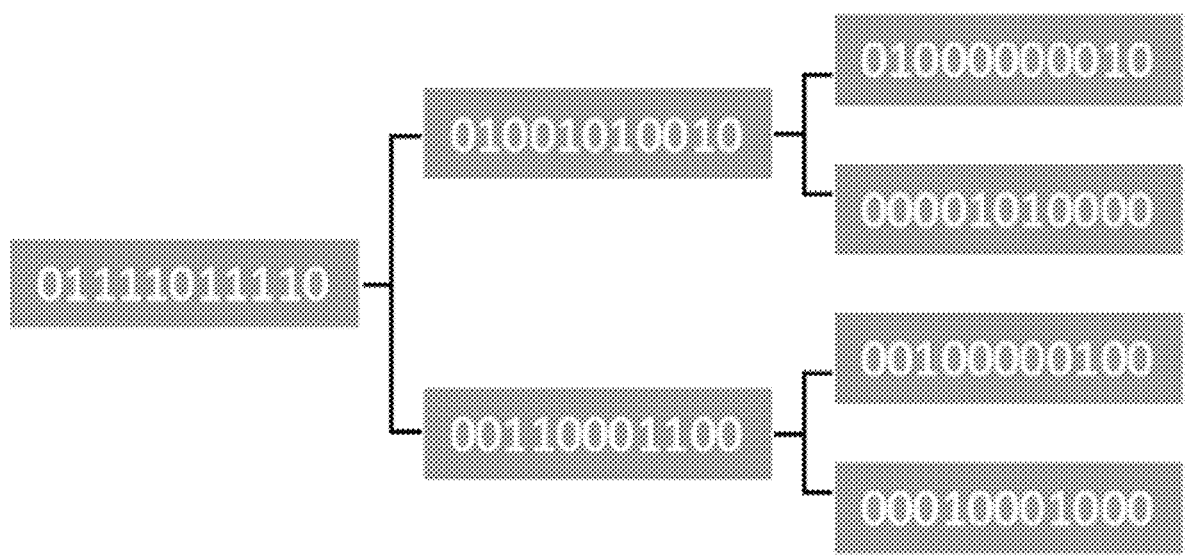
FIG. 4A is a schematic representation of an edge code in which '1' in the second to fifth digits in each code corresponds to an indentation or bump on a tile edge in square tile in FIG. 5C in which the three rows correspond to the edge codes used in stages 1 to 3, according to embodiments of the present disclosure.
Figure 4B:
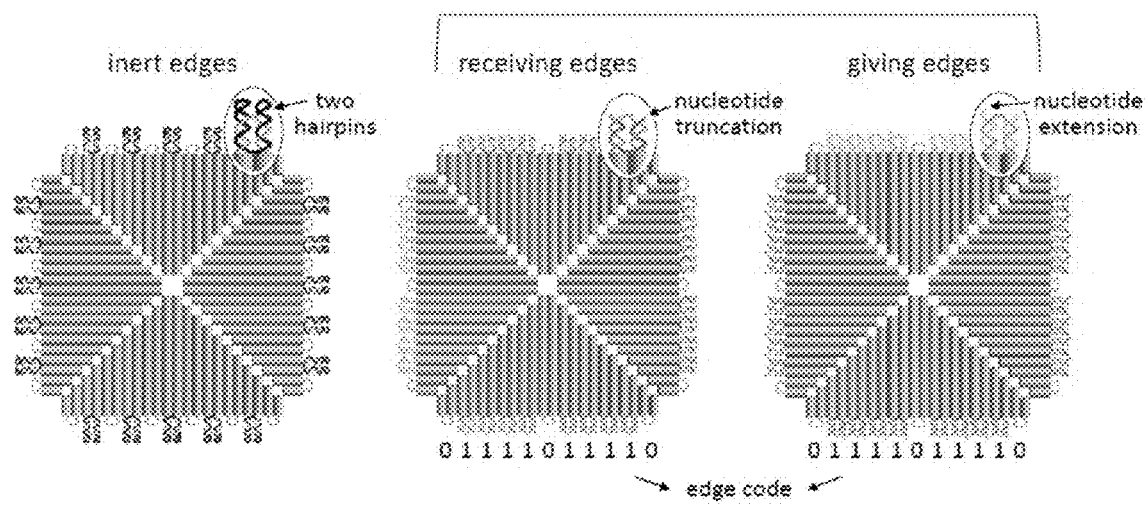
FIG. 4B depicts a square polynucleotide tile (DNA origami tile) according to embodiments of the present disclosure, the tile having four edges designated as north (N), east (E), south (S) and west (W), which each edge has a maximum of eleven staples, where because the four triangles composing the square tile are folded from different parts of the M13mp18 DNA scaffold, the staples on the four edges naturally have different sequences, where "Inert edges" are created using five edge staples that are each capped with two hairpins to inhibit their interactions with other edge staples, the Inert edge staples are colored black, and six edge staples are left out and the remaining scaffold loops are colored gray; where there are two types of "active edges": "receiving edges" are created using eight or less edge staples that each has a two-nucleotide truncation on the 3' end; "giving edges" are created using eight or less edge staples that each has a two-nucleotide extension on the 5' end. An "edge code" is associated with each receiving or giving edge: in which the code consists of eleven 0s and 1s, and each 0 corresponds to a scaffold loop and each 1 corresponds to a staple. Receiving staples on the north, east, south and west edges are colored blue, green, orange and yellow, respectively. Giving staples are colored based on the sequence identity of the extension: extensions that are complementary to the truncations on the north, east, south and west edges are colored blue, green, orange and yellow, respectively. Although a giving edge can be complementary to any receiving edge, we only use north giving to west, east giving to north, south giving to east, and west giving to south in the design of fractal assembly. Abstract tiles are used to simplify the illustration. The edge colors in an abstract tile correspond to the staple colors in an origami tile. Each indentation corresponds to a 1 in an edge code for a receiving edge. Each bump corresponds to a 1 in an edge code for a giving edge. In fractal assembly, palindromic edge codes are used that having three 0s at fixed locations, and therefore, only the second to fifth digits are needed to infer any edge code, and only the 1s in these four digits are shown as indentations or bumps in an abstract tile.
Figure 4B:
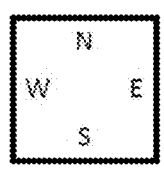
Figure 4B:
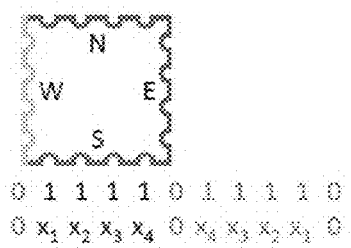
Figure 4B:
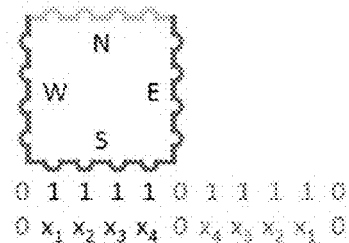
Figure 4C:
FIG. 4C is a schematic representation of an edge code in which the five rows correspond to the edge codes used in stages 1 to 5, according to embodiments of the present disclosure.

The third embodiment is the 'edge code' rule. As shown in FIG. 4A, each code consists of eleven '0's and '1's, defining one edge of a tile. Each 0 corresponds to a scaffold loop and each 1 to a staple as depicted in FIG. 4B. In this case, palindromic codes were used to reduce asymmetric structural fluctuation of the DNA origami tiles and to promote stability of the self-assembled structures. Stage 1 of a fractal assembly uses a code of eight 1s. For each subsequent stage, the number of tile edges participating in the desired array interactions doubles. Therefore, to resolve the challenge involved in the annealing process discussed above, we split the 1 s in each edge code from the previous stage to generate two new edge codes, each of which have half of the 1s from the previous code (FIG. 4A). This way, the total number of edge staples participating in the desired interactions between tiles or arrays at any stage will be constant, and the locations of the edge staples will be more spread out for a later stage. As a result, the total binding energy between tiles or arrays will decrease with increased spacing between individual hybridization locations. The melting temperature of the structures that are self-assembled in each stage will thus decrease sequentially, which makes it possible to find an annealing temperature for each stage that is high enough to break the spurious interactions between the products from the previous stage, but low enough that these products do not fall apart.

For self-assembly of an 8 by 8 square tile array as shown in FIG. 5C, the following annealing stages were carried out:

Stage 0: anneal the monomer polynucleotide tiles (i.e. single origami tiles) from 90 to 20° C. at 6 sec per 0.1 C.

After the Stage 0 anneal, a five-fold excess (relative to the concentration of the staple strands) of a full set of 44 negation strands were added to each type of DNA origami tile and quickly cooled down from 50 to 20° C. at 2 sec per 0.1° C.

Stage 1: anneal the 2 by 2 arrays by mixing equal volumes of four individual tiles and annealing from 55 to 45° C. at 2 min per 0.1 C (slower phase) and from 45 to 20° C. at 6 sec per 0.1 C (faster phase). The total annealing time of Stage 1 was roughly 3.5 hours.

Stage 2: anneal the 4 by 4 arrays by mixing equal volumes of four 2 by 2 arrays obtained in the previous step and annealing from 45 to 35° C. at 8 min per 0.1 C (slower phase) and from 35 to 20° C. at 6 sec per 0.1 C (faster phase). The total annealing time of Stage 2 was roughly 13.5 hours.

Stage 3: anneal the 8 by 8 array by mixing equal volumes of four 4 by 4 arrays obtained in the previous step and annealing from 35 to 25° C. at 32 min per 0.1 C (slower phase) and from 25 to 20° C. at 6 sec per 0.1 C (faster phase). The total annealing time of Stage 2 was roughly 53.5 hours.

For arrays with patterns, a 10-fold excess of poly-A strand was added to the arrays before imaging, allowing at least ten minutes for the poly-A strand to hybridize to the poly-T staple extensions at room temperature.

Materials and Methods. For the Single-stranded M13mp18 DNA (scaffold strand) was purchased from Bayou Biolabs (catalog \#P-107) at 1~g/L in 1× TE buffer (10~mM Tris-HCl, 1~mM EDTA, pH 8.0).

Staple strands (sequences listed in Supplementary Tables 1 to 5 of Tikhomirov et al., 2017, supra) were purchased unpurified from Integrated DNA Technologies in 1×TE buffer (pH 8.0) at 100 uM each.

Negation strands (sequences listed in Supplementary Table 6) that are complementary to the edge staples were purchased at 200 uM each.

The strands were diluted to 15 uM in 1×TE buffer and loaded into Echo qualified 384-well source microplate (Labcyte).

Example 2

Triangular and hexagonal tile arrays as described herein and shown in FIGS. 1, 2A, and 2B were assembled as described in the attached APPENDIX.

While the present disclosure has been illustrated and described with reference to certain exemplary embodiments, those of ordinary skill in the art will understand that various modifications and changes may be made to the described embodiments without departing from the spirit and scope of the present disclosure, as defined in the following claims.

What is claimed is:

1. A nucleic acid microstructure comprising:
an n×n array of $n^2$ polynucleotide square tiles, each of the $n^2$ polynucleotide square tiles comprising:
  a single-stranded helical polynucleotide scaffold of a known sequence; and
  a plurality of selected single-stranded polynucleotide staple strands being at least partially complementary to the polynucleotide scaffold and annealed to the polynucleotide scaffold to form a square tile shape;
the n×n array of $n^2$ polynucleotide square tiles further comprising a plurality of 2×2 sub-arrays, each of the plurality of 2×2 sub-arrays comprising a set of four polynucleotide square tiles, each of the four polynucleotide square tiles having p number of inside single-tile extended polynucleotide staple strands or p number of inside single-tile truncated polynucleotide staple strands, the inside single tile extended polynucleotide staple strands being annealed with the inside single-tile truncated polynucleotide staple strands to form the plurality of 2×2 sub-arrays, wherein each of the plurality of 2×2 subarrays comprise four two-tile edges and any inside two-tile edges in any of the plurality of 2×2 sub-arrays have less than p number of inside two-tile extended polynucleotide staple strands or less than p number of inside two-tile truncated polynucleotide staple strands, where the inside two-tile extended polynucleotide staple strands are annealed with the inside two-tile truncated polynucleotide staple strands to form at least one 4×4 subarray.

2. The nucleic acid microstructure of claim 1, wherein n is 2, 4, or 8.

3. The nucleic acid microstructure of claim 1, wherein the single-stranded helical polynucleotide scaffold is derived from M13mp18 DNA.

4. A method of assembling the nucleic acid microstructure of claim 1, the method comprising:
- selecting a value for n in the n by n array of $n^2$ polynucleotide square tiles;
- determining a number of subarray annealing stages as log 2 n; and
- preparing $n^2$ mixtures for each of the $n^2$ polynucleotide square tiles, each mixture comprising the single-stranded helical polynucleotide scaffold and corresponding single-stranded polynucleotide staple strands specific to each of the $n^2$ polynucleotide square tiles out of the plurality of selected single-stranded polynucleotide staple strands.

* * * * *